(12) United States Patent
Al-Dhabi et al.

(10) Patent No.: US 10,064,841 B1
(45) Date of Patent: Sep. 4, 2018

(54) ISOANDROGRAPHOLIDE-19-PROPIONATE FOR TREATMENT OF NON-ALCOHOLIC FATTY LIVER DISEASE (NAFLD)

(71) Applicant: KING SAUD UNIVERSITY, Riyadh (SA)

(72) Inventors: Naif Abdullah Al-Dhabi, Riyadh (SA); Savarimuthu Ignacimuthu, Tamil Nadu (IN); P. Pandikumar, Tamil Nadu (IN); Erenius Toppo, Tamil Nadu (IN); Sylvester Darvin, Tamil Nadu (IN)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/864,704

(22) Filed: Jan. 8, 2018

(51) Int. Cl.
*A61P 1/16* (2006.01)
*A61K 31/365* (2006.01)

(52) U.S. Cl.
CPC ............... *A61K 31/365* (2013.01); *A61P 1/16* (2018.01)

(58) Field of Classification Search
CPC ........................................................ A61P 1/16
See application file for complete search history.

(56) References Cited

U.S. PATENT DOCUMENTS

| 8,445,533 B2 | 5/2013 | Liu et al. |
| 2012/0015923 A1 | 1/2012 | Wong |
| 2015/0150893 A1 | 6/2015 | Xu |

FOREIGN PATENT DOCUMENTS

| CN | 101029046 | 9/2007 |
| CN | 101560198 | 10/2009 |

OTHER PUBLICATIONS de Santana Souza et al., "Structure-Activity Relationship of Terpenes with Anti-Inflammatory Profile—A Systematic Review", Basic & Clinical Pharmacology & Toxicology (2014), vol. 115(3), pp. 244-256.

Erenius Toppo et al., "Effect of Two Andrographolide Derivatives on Cellular and Rodent Models of Non-Alcoholic Fatty Liver Disease", Biomedicine & Pharmacotherapy (2017), vol. 95, pp. 402-411.

"3,19-Dipropionyl isoandrographolide", National Center for Biotechnology Information, PubChem Substance Database, SID=163653255.

"3-Propionyl isoandrographolide", National Center for Biotechnology Information, PubChem Compound Database, CID=49841564.

*Primary Examiner* — Andrew D Kosar
*Assistant Examiner* — John S Kenyon
(74) *Attorney, Agent, or Firm* — Richard C. Litman

(57) ABSTRACT

Isoandrographolide-19-propionate for treatment of non-alcoholic fatty liver disease (NALFD) relates to the compound isoandrographolide-19-propionate (IAN-19P), having the structural formula:

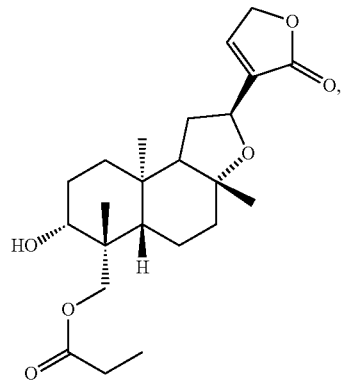

and pharmaceutically acceptable salts thereof. The compound is synthesized by reaction of isoandrographolide with anhydrous propionic acid in the presence of N,N'-dicyclohexylcarbodiimide and 4-dimethylaminopyridine. In vitro testing shows that isoandrographolide-19-propionate has lower toxicity than andrographolide, but has significantly high activity at a concentration of 50 µM. IAN-19P produced normal triglyceride levels and significantly lowered lipoperoxide formation in palmitate-oleate induced steatotic HepG2 cells, and also lowered ALT leakage from the treated cells.

7 Claims, 7 Drawing Sheets

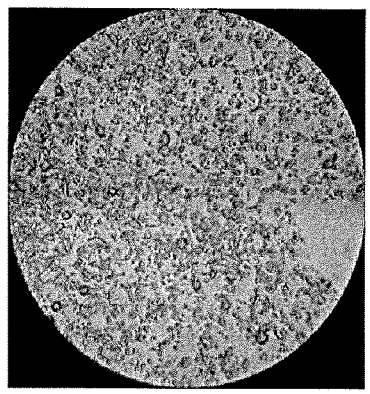
FIG. 2C Fenofibrate
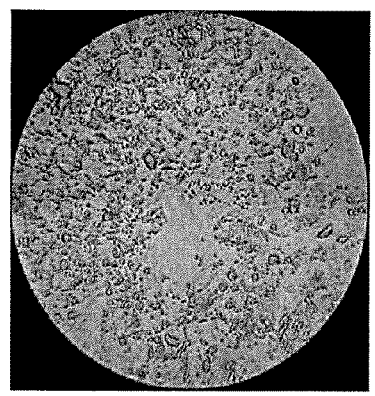
FIG. 2F Isoandrographolide-19-propionate
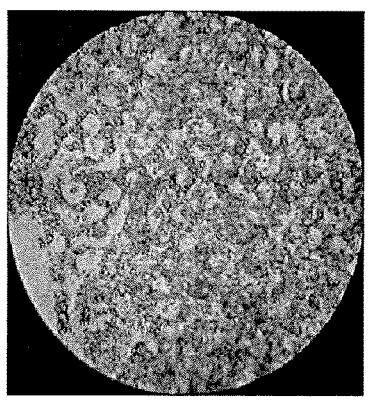
FIG. 2B Fatty Acid Treated
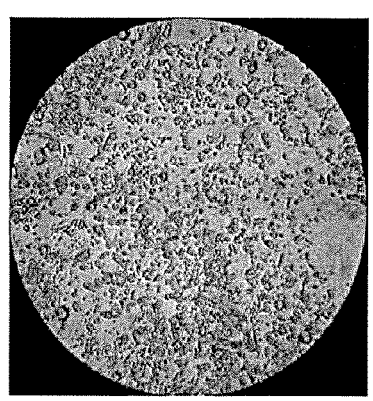
FIG. 2E Isoandrographolide
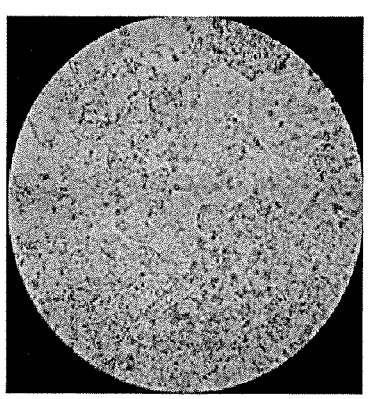
FIG. 2A Normal Control
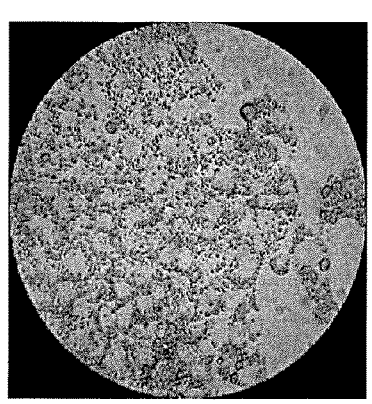
FIG. 2D Andrographolide

ISOANDROGRAPHOLIDE-19-PROPIONATE FOR TREATMENT OF NON-ALCOHOLIC FATTY LIVER DISEASE (NAFLD)

BACKGROUND

1. Field

The disclosure of the present patent application relates to andrographolide derivatives, and particularly to isoandrographolide-19-propionate for treatment of non-alcoholic fatty liver disease (NALFD), the use of the compound in hepatoprotective applications, and methods of synthesizing the compound.

2. Description of the Related Art

Andrographolide (AN) is a major constituent of an important medicinal plant, *Andrographis paniculata*. Andrographolide is particularly effective when used in treating various diseases, including some hepatopathies, and has come of interest as a naturally derived product that may potentially be effective in treating various hepatopathies and useful as a hepatoprotective agent.

Non-Alcoholic Fatty Liver Disease (NAFLD) is a common liver disease, and is becoming more prevalent with the increasing incidence of metabolic syndromes. NAFLD is a progressive liver disease leading to fibrosis, cirrhosis, and hepatocellular carcinoma, even in the absence of significant alcohol consumption. However, current therapeutic options to treat NAFLD or Non-Alcoholic Steato-Hepatitis (NASH) are only limited, and medications with long term efficacy that beneficially affect fibrosis are lacking.

Thus, isoandrographolide-19-propionate for treatment of non-alcoholic fatty liver disease (NALFD) solving the aforementioned problems is desired.

SUMMARY

Isoandrographolide-19-propionate for treatment of non-alcoholic fatty liver disease (NALFD) relates to the compound isoandrographolide-19-propionate (IAN-19P), having the structural formula:

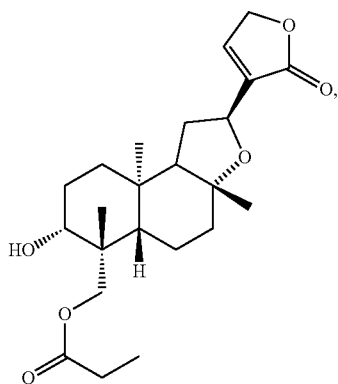

and pharmaceutically acceptable salts thereof. The compound is synthesized by reaction of isoandrographolide with anhydrous propionic acid in the presence of N,N'-dicyclohexylcarbodiimide and 4-dimethylaminopyridine. In vitro testing shows that isoandrographolide-19-propionate has lower toxicity than andrographolide, but has significantly high activity at a concentration of 50 µM. IAN-19P produced normal triglyceride levels and significantly lowered lipoperoxide formation in palmitate-oleate induced steatotic HepG2 cells, and also lowered ALT leakage from the treated cells.

These and other features of the present disclosure will become readily apparent upon further review of the following specification and drawings.

BRIEF DESCRIPTION OF THE DRAWINGS

FIG. 2A is a photomicrograph showing a normal control of HepG2 cells supplemented with media containing only BSA (bovine serum albumin).

FIG. 2B is a photomicrograph showing a negative control of HepG2 cells supplemented with media containing PO-BSA (palmitate-oleate bovine serum albumin).

FIG. 2C is a photomicrograph showing a positive control of palmitate-oleate induced steatotic HepG2 cells treated with fenofibrate (12.5-50 µM).

FIG. 2D is a photomicrograph showing palmitate-oleate induced steatotic HepG2 cells treated with andrographolide.

FIG. 2E is a photomicrograph showing palmitate-oleate induced steatotic HepG2 cells treated with isoandrographolide.

FIG. 2F is a photomicrograph showing palmitate-oleate induced steatotic HepG2 cells treated with isoandrographolide-19-propionate.

Similar reference characters denote corresponding features consistently throughout the attached drawings.

DETAILED DESCRIPTION OF THE PREFERRED EMBODIMENTS

Figure 1A:
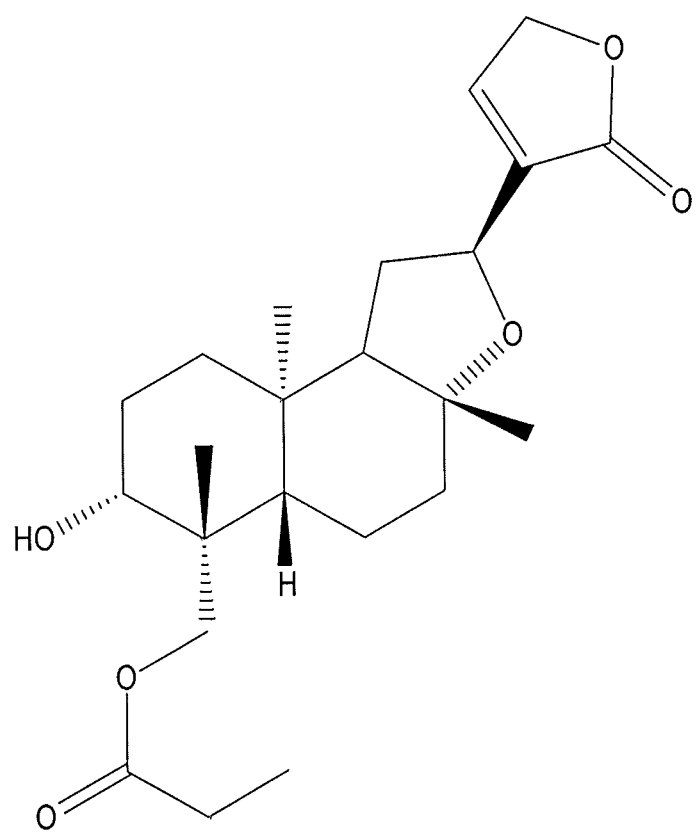
FIG. 1A is the structural formula of the compound isoandrographolide-19-propionate (IAN-19P).

Isoandrographolide-19-propionate for treatment of non-alcoholic fatty liver disease (NALFD) relates to the compound isoandrographolide-19-propionate (IAN-19P), having the structural formula:

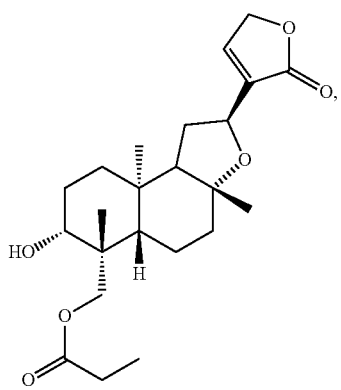

and pharmaceutically acceptable salts thereof. The compound is synthesized by reaction of isoandrographolide with anhydrous propionic acid in the presence of N,N'-dicyclohexylcarbodiimide and 4-dimethylaminopyridine. In vitro testing shows that isoandrographolide-19-propionate has lower toxicity than andrographolide, but has significantly high activity at a concentration of 50 μM. IAN-19P produced normal triglyceride levels and significantly lowered lipoperoxide formation in palmitate-oleate induced steatotic HepG2 cells, and also lowered ALT leakage from the treated cells.

In the Description, the following abbreviations are used. ALT—Alanine transaminase; AN—Andrographolide; $CDCl_3$-deuterated chloroform; DMEM—Dulbecco's Minimal Essential Medium; DMSO—Dimethyl sulfoxide; FBS—Fetal Bovine Serum; FT-IR—Fourier Transform Infra-red Spectroscopy; IAN—isoandrographolide; IAN-19P—Isoandrographolide 19 propionate; KBr—Potassium Bromide; MTT—[3-(4,5-dimethylthiazol-2-yl)-2,5-diphenyltetrazolium bromide]; NMR—Nuclear Magnetic Resonance; ORO—Oil Red O; PO-BSA—palmitate, oleate—BSA mixture; TBARS—Thiobarbituric acid reactive substances; TMS—Tetramethylsilane.

In the following examples, andrographolide (AN) was purchased from Natural Remedy Private Limited, Bengaluru, India. Solvents and reagents of analytical grade were purchased from Qualigens. FT-IR spectrum was recorded on a Perkin-Elmer FT-IR (Spectrum Two) in KBr disc. $^1H$ and $^{13}C$ NMR spectra were recorded on Bruker AV-500 (500 and 125 MHz) with $CDCl_3$ as the solvent. Chemical shifts were recorded as δ values in parts per million (ppm), with TMS as the internal standard. Sodium oleate, sodium palmitate and fenofibrate were purchased from Sigma Aldrich; DMEM and FBS were purchased from Gibco. Antibiotic-antimycotic mixture, trypsin, DMSO, ORO, MTT dye, and all other chemicals of analytical grade were obtained from Hi-Media chemicals. Triglyceride and protein estimation kits were purchased from Merck and Bio-Rad, respectively. ALT and TBARS estimation kits were purchased from Himedia. HepG2 cells were obtained from National Center for Cell Sciences, Pune (India) and cultured in 5% $CO_2$ incubator at 37° C. using DMEM supplemented with FBS (10%), penicillin (100 U/mL) and streptomycin (100 μg/mL). The cells were sub-cultured at 75% confluence by total media replacement using 0.25% (w/v) trypsin—0.53 mM EDTA every 2-3 days. The DMSO was used as the vehicle and its level was set as 0.01% for all the in vitro bioassays.

Example 1

Synthesis of Isoandrographolide from Andrographolide

To 1 M andrographolide, 2.5 M conc. HCl was added and the mixture was stirred at room temperature for 24 h. The whole solution was poured into ice cold water and extracted with dicholoromethane. The combined organic layer was washed twice with water and dried over anhydrous $Na_2SO_4$. Crystallization with dichloromethane yielded IAN (yield: 98%; purity: 98.5%).

Example 2

Preparation of Isoandrographolide 19 Propionate (IAN-19P)

To 1.2 M anhydrous propionic acid (also called propanoic acid herein) and 2.0 M N,N'-dicyclohexylcarbodiimide, 30 mL of dichloromethane was added and stirred for 30 minutes. Then, 1 mole of isoandrographolide and 0.0.2 M of 4-dimethylaminopyridine were added. The reaction mixture was stirred for 30 min at room temperature, and the reaction was monitored using thin layer chromatography (TLC). Once the reaction was completed, the reaction mixture was filtered, washed with water, dried over anhydrous sodium sulfate and concentrated. The concentrate was packed in a silica gel column (Avera, 400 mesh) in a flash column and eluted first with hexane, then with hexane and dichloromethane mixture, and finally with 5% methanol in dichloromethane. The elutants at 5% methanol in dichloromethane yielded IAN-19P as a colorless powder (yield: 95%, purity 98.5%).

Figure 1B:
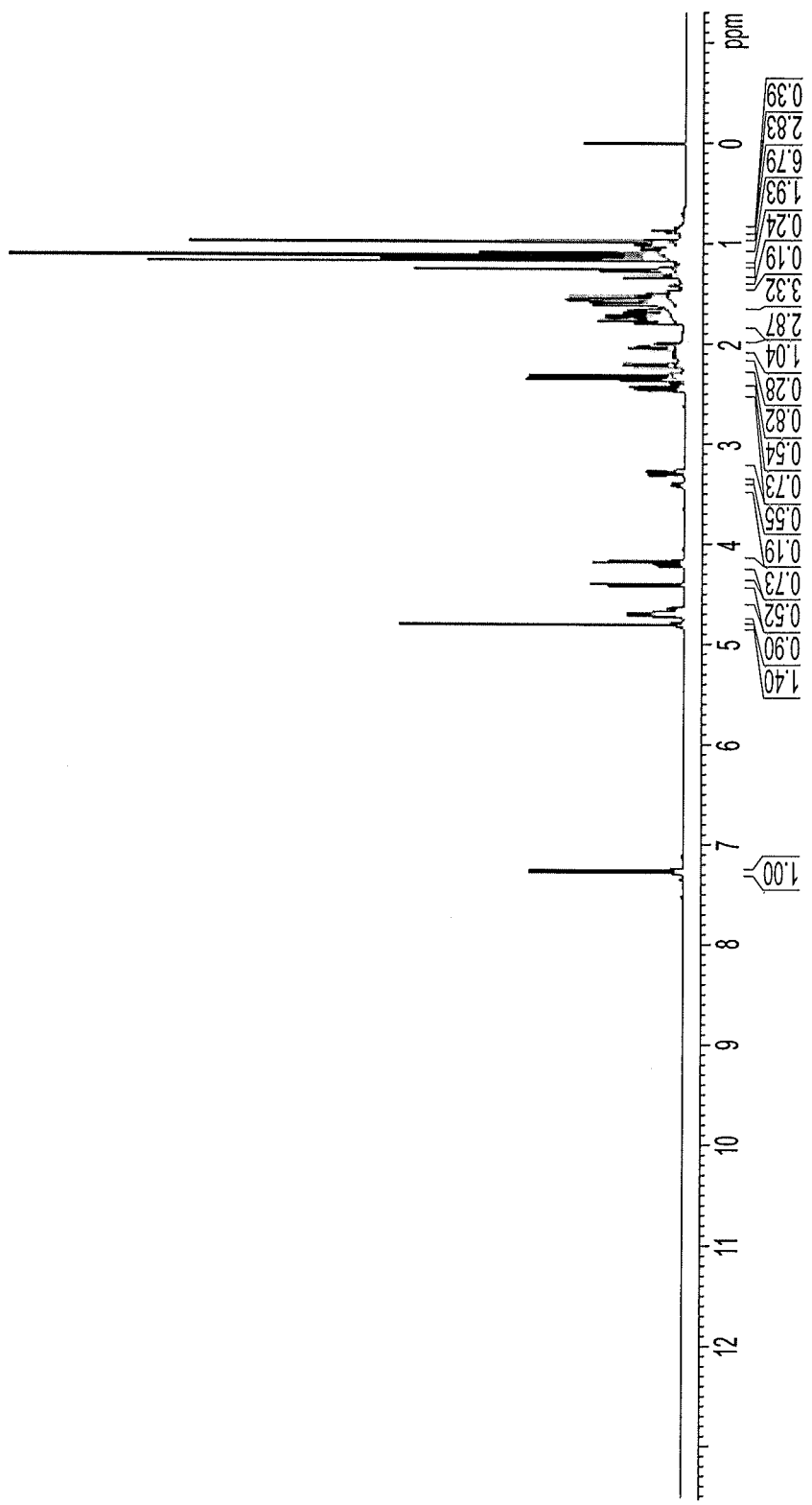
FIG. 1B is the $^1$H NMR spectrum of IAN-19P.
Figure 1C:
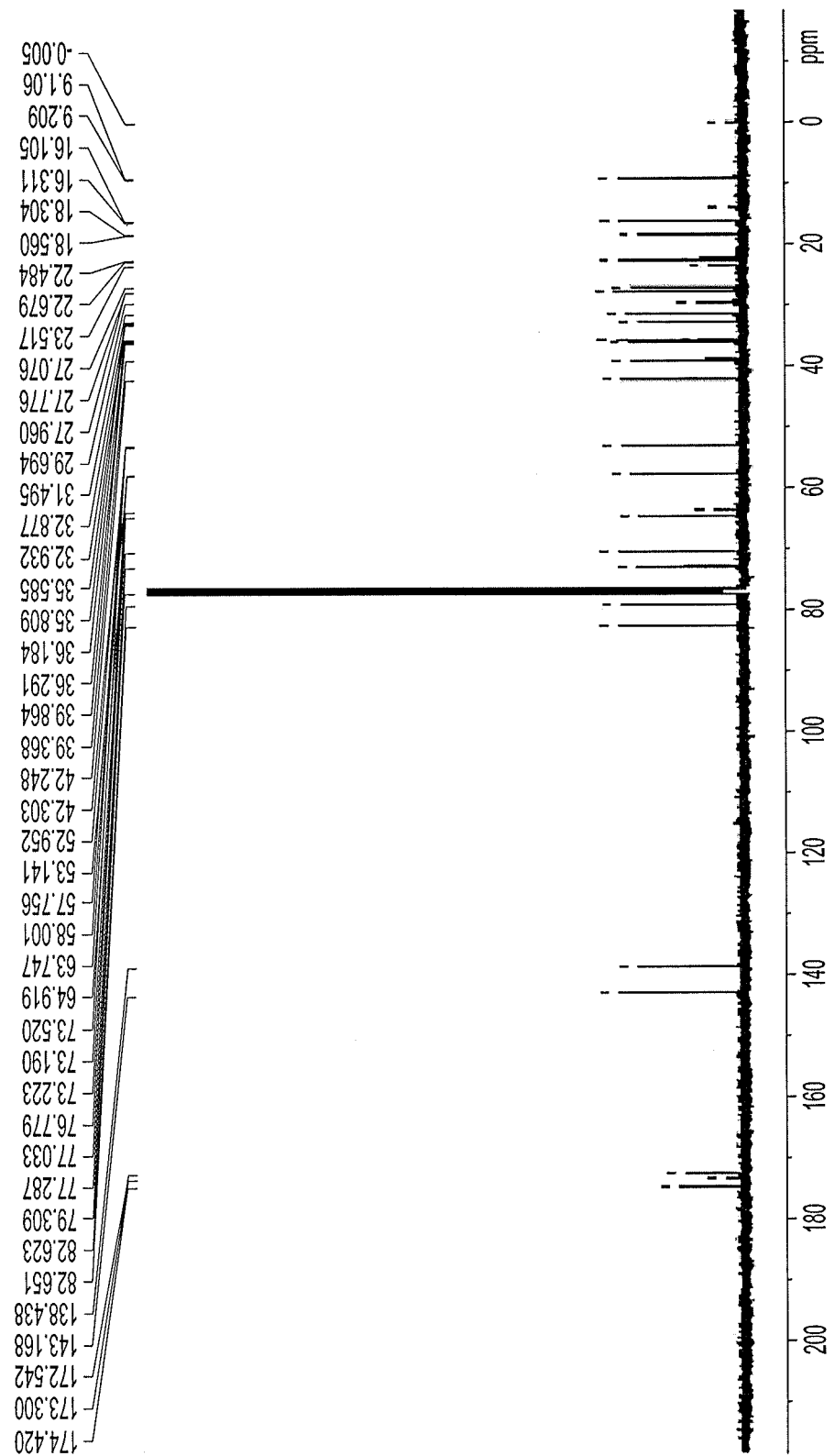
FIG. 1C is the $^{13}$C NMR spectrum of IAN-19P.
Figure 1D:
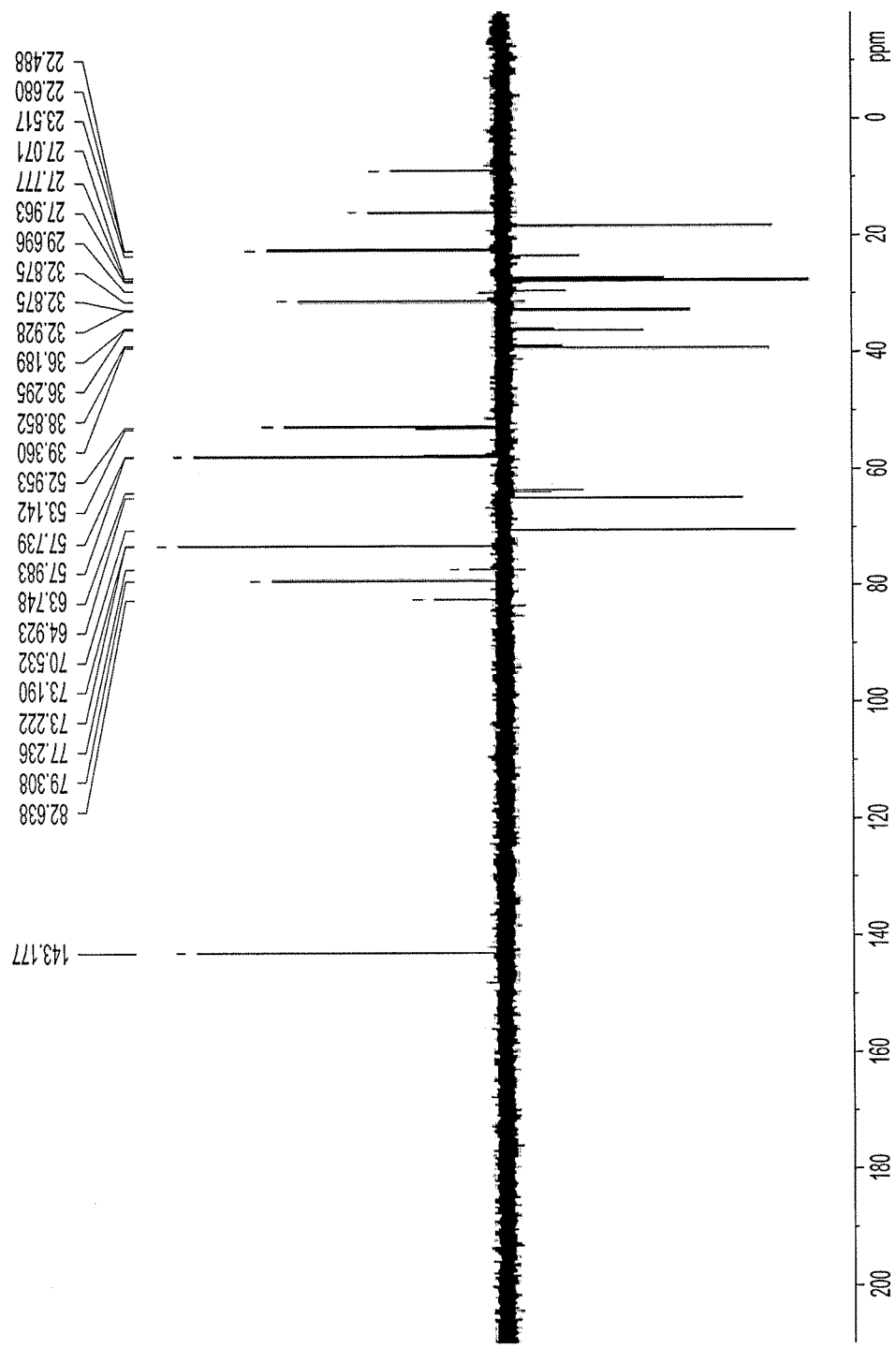
FIG. 1D is the $^{13}$C DEPT NMR spectrum of IAN-19P.
Figure 1E:
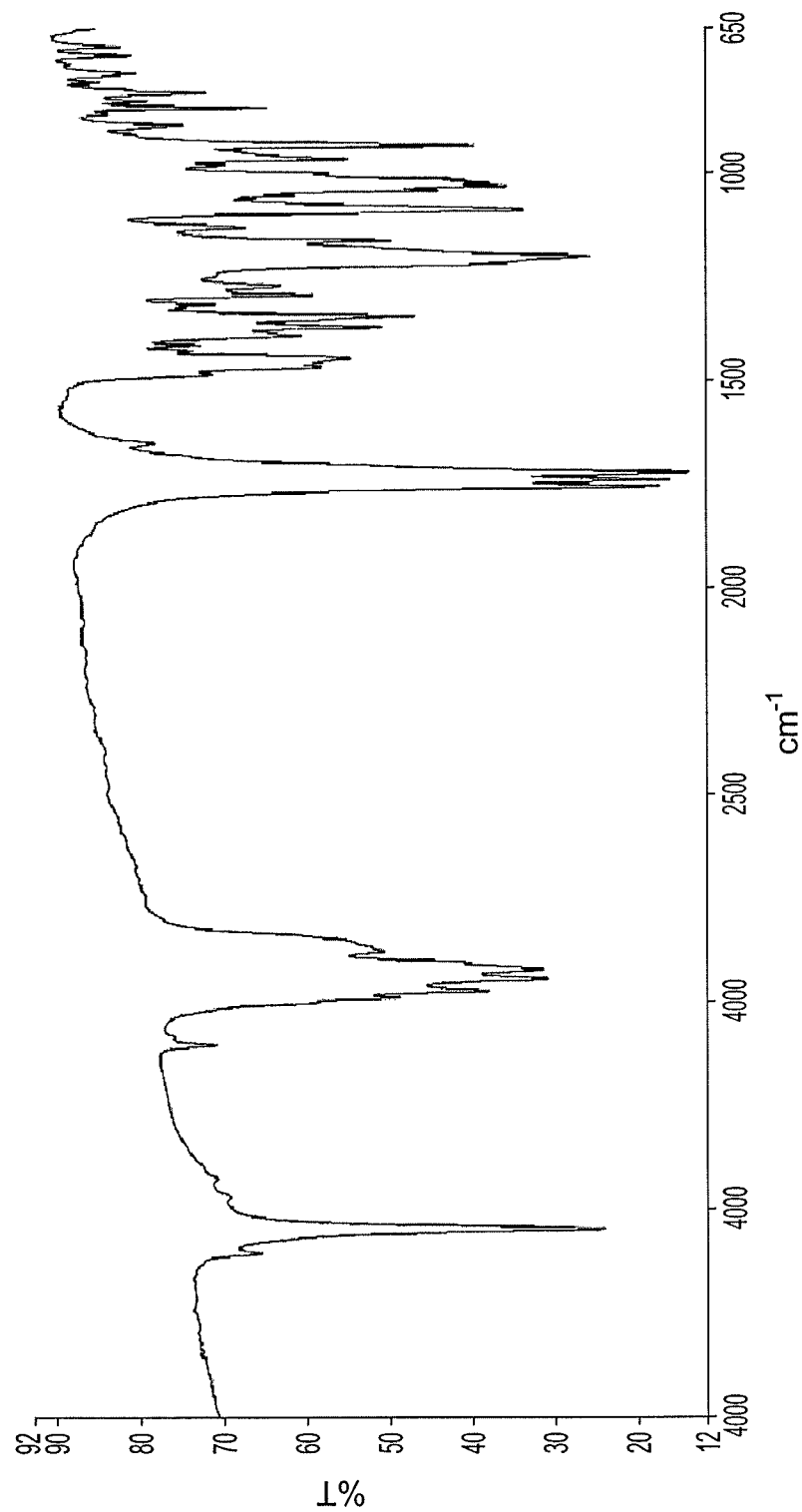
FIG. 1E is the FT-IR spectrum of IAN-19P.

The structure of the compound is given in FIG. 1A. The $^1H$ NMR spectrum of IAN-19P is shown in FIG. 1B. FIG. 1C is the $^{13}C$ NMR spectrum of IAN-19P. FIG. 1D is the $^{13}C$ DEPT NMR spectrum of IAN-19P. FIG. 1E is the FT-IR spectrum of IAN-19P.

Isoandrographolide 19-propionate (IAN-19P) is obtained in colorless solid form; mp: 170-172° C.; it analyzed for $C_{23}H_{34}O_6(M^+ m/z\ 406)$, gave single spot (Rf=0.55) on TLC over silica gel with chloroform-methanol (19:1) as the developing system (visualization: 10% alcoholic $H_2SO_4$ heated at 110° C. for three min). IR ($v_{max}$ KBr, $cm^{-1}$) 3550 (hydroxyl), 2945, 2879, 1755 (α, β unsat. lactone carbonyl), 1739 (propionate carbonyl), 1447, 1372, 1345, 1201 (propionate C—O—C), 1088, 1030 and 933; $^1H$ NMR (δ$CDCl_3$, 500 MHz): 0.98 (3H, s, H-20), 1.11 (3H, s, H-17), 1.17 (3H, s, H-18), 1.11 (3H, t, J=8.0 Hz, OCOCH$_2$C$\underline{H}_3$), 2.34 (2H, q, J=8.0 Hz, OCOC$\underline{H}_2$CH$_3$), 3.29 (1H, dd, J=11.5 and 4.0 Hz, H-3), 2.03 (1H, m, H-11a), 2.45 (1H, dd, J=13.5 and 8.5 Hz, H-11b), 4.19 (1H, d, J=11.5 Hz, H-19a), 4.41 (1H, d, J=11.5 Hz, H-19b), 4.72 (1H, m, H-12), 4.81 (2H, m, H-15) and 7.28 (1H, m, H-14); $^{13}C$ NMR (δ$CDCl_3$ 125 MHz): 36.3 (C-1), 27.07 (C-2), 79.31 (C-3), 42.25 (C-4), 52.95 (C-5), 18.56 (C-6), 39.38 (C-7), 82.65 (C-8), 58.00 (C-9), 35.81 (C-10), 32.88 (C-11), 73.22 (C-12), 138.44 (C-13), 143.17 (C-14), 70.53 (C-15), 172.54 (C-16), 31.49 (C-17), 22.68 (C-18), 64.92 (C-19), 16.11 (C-20), 174.42 (OCOCH$_2$CH$_3$), 27.78 (OCO$\underline{C}$H$_2$CH$_3$) and 9.11 (OCOCH$_2$$\underline{C}$H$_3$).

Example 3

MTT Toxicity Assay

The cytotoxic effect was analyzed by using the MTT assay as described by Mosmann, J. Immunol Methods.

65:55-63 (1983), with minor modification. HepG2 cells were seeded at 5×10³ cells/well into a 96-well plate and incubated for 24 h. Spent media was then replaced with fresh media containing test materials (100-500 µM) dissolved in DMSO. Vehicle control cells were treated only with DMSO. The plates were incubated in a $CO_2$ incubator for 24 h. The spent media was then replaced with sterile MTT solution (5 mg/mL in PBS at pH—7.4; 100 µL/well) and incubated for another 3 h. The unreacted MTT dye was removed, and the formazan crystals were dissolved with DMSO (200 µL/well) and kept in dark for 30 min. The resulting purple color was quantified by measuring absorbance at 570 nm. The assays were performed thrice and the results were expressed in percentage in comparison to vehicle-treated cells. The following formula was used for calculation.

$$\text{Cell population growth percentage} = \left(\frac{A_{570(test\ material)}}{A_{570(control)}}\right) \times 100$$

$GI_{50}$ values were calculated using linear regression analysis.

The MTT assay showed that IAN-19P had comparatively lower toxicity than AN (see Table 1, where $GI_{50}$ is the concentration for 50% of maximal inhibition of cell proliferation).

TABLE 1

MTT assays—toxicity of compounds

| Name of the compound | $GI_{50}$ (mM) | $R^2$ | P |
|---|---|---|---|
| AN | 0.254 | 0.704 | 0.001 |
| IAN | 23.70 | 0.126 | 0.010 |
| IAN-19P | 27.00 | 0.304 | 0.123 |

Example 4

Induction of Steatosis in HepG2 Cell Lines Using Palmitate, Oleate-BSA (PO-BSA) Mixture Induction of steatosis was done in accordance with the protocol of Hetherington and coworkers, Cell Physiol Biochem. 39:1648-62 (2016), with slight modification. HepG2 cells were loaded in 24-well cell culture plates at a density of 4×10⁴ cells/well and kept overnight. On the next day, the media were replaced with fresh media containing PO-BSA at 1 mM concentration, with or without test materials (12.5-50 µM) dissolved in DMSO. The cells supplemented with media containing only BSA (instead of PO-BSA) and treated with DMSO (FIG. 2A) served as the normal control. The cells supplemented with media containing PO-BSA and treated with DMSO (FIG. 2B) served as negative control. Fenofibrate (12.5-50 µM) (FIG. 2C) was used as the positive control. After 24 h of treatment, the cells were taken for the analyses.

IAN-19P showed a significantly lower $EC_{50}$ value (five times less) ($EC_{50}$ value refers to the concentration of a substance that induces a response halfway between the baseline and maximum after a specified exposure time) than AN and IAN in the reduction of ORO stain in the palmitate-oleate induced steatotic HepG2 cells (FIGS. 2D-2F and Table 2). Table 2: $EC_{50}$ values of andrographolide and its derivatives on the reduction of Oil Red O stain in steatotic HepG2 cells

TABLE 2

$EC_{50}$ values for reduction of Oil Red O stain in steatotic HepG2 cells

| Name of the compound | $EC_{50}$ (mM) | $R^2$ | P |
|---|---|---|---|
| AN | 43.32 | 0.092 | 0.225 |
| IAN | 27.00 | 0.228 | 0.116 |
| IAN-19P | 8.92 | 0.478 | 0.012 |

Example 5

Antihyperlipidemic Assay

After treatment, the amount of lipids accumulated into the cells was measured using ORO staining. Briefly, 24 h after treatment, the spent media was removed and the cells were fixed by incubating them with 10% formalin in PBS for 1 h at room temperature. Each well was washed with 60% aqueous isopropanol and was allowed to dry. Then, the cells were incubated with ORO solution for 10 min and washed with deionized water to remove excess dye. Cell morphology was assessed and photographed (400×) using an inverted microscope. The ORO stain was eluted with 100% isopropanol and measured at 500 nm. Empty wells were stained and used as reagent blank and 100% isopropanol as control blank. The results were expressed as the percentage of absorbance of the sample to the absorbance of the control blank.

After treatment, the cells were harvested and lysed using 1×PBS under sonication at 3× for five second intervals at 40V setting over ice. The cell lysates were taken and estimated for TG and protein using commercial spectrophotometric kits. TG levels were normalized to the protein content, and results were expressed as mg TG/g protein. The MDA levels in the cell lysate were estimated using a commercial spectrophotometric kit. The levels of ALT were measured in the spent media, and cell lysate and percent ALT leakage was calculated using the following formula:

$$\% ALT\ release = \left(\frac{ALT\text{ level in the supernatant}}{ALT\text{ level in the supernatant} + ALT\text{ level in the lysate}}\right) \times 100$$

In the palmitate-oleate induced steatotic HepG2 cells, the treatment with IAN-19P at 50 µM concentration showed significantly high activity. The triglyceride level had come to normal, and this effect is statistically superior to that of AN and IAN (see FIG. 3). The treatment with IAN-19P also significantly lowered the lipoperoxide formation in the palmitate-oleate induced steatotic HepG2 cells better than AN and IAN at 50 µM concentration (see FIG. 4). The treatment with IAN-19P also lowered ALT leakage from the treated cells (see FIG. 5). The in vitro test results suggest that isoandrographolide-19-propionate and pharmaceutically acceptable salts thereof has utility as the active ingredient of a pharmaceutical preparation for the prevention or reduction of the incidence of non-alcoholic fatty liver disease, and for the treatment of non-alcoholic fatty liver disease, including hepatopathies and hepatocellular disorders and diseases incident thereto. Furthermore, the invention includes an embodiment comprising a pharmaceutical agent for reducing the incidence of non-alcoholic fatty liver disease and/or for treatment of non-alcoholic fatty liver disease and hepatocellular disorders and diseases incident thereto, comprising a pharmaceutical composition having isoandrographolide-19-propionate as its active ingredient. An embodiment of the invention includes a method of treating non-alcoholic fatty liver disease, comprising the step of administering an effective amount of a pharmaceutical agent to a patient in need thereof, the pharmaceutical agent including isoandrographolide-19-propionate, or a pharmaceutically acceptable salt thereof.

Figure 3:
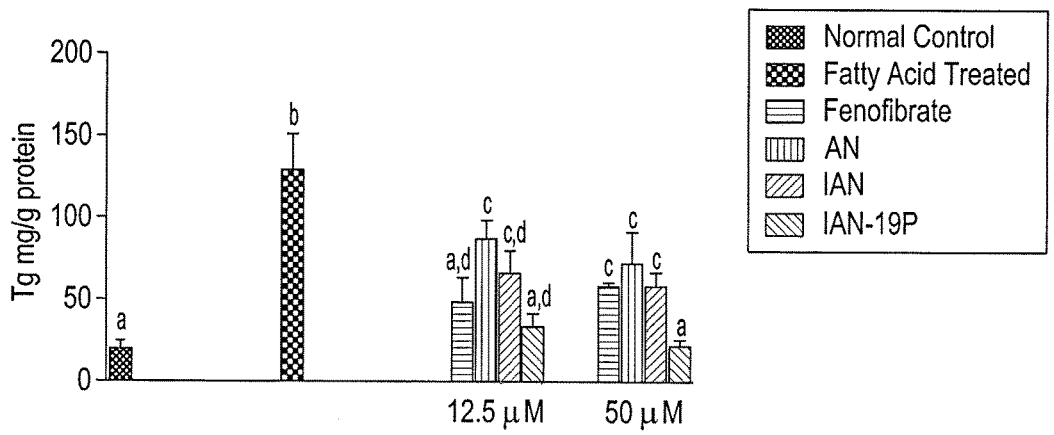
FIG. 3 is a chart showing the effect of AN, IAN and IAN-19P on triglyceride accumulation of palmitate-oleate induced HepG2 cell lines.
Figure 4:
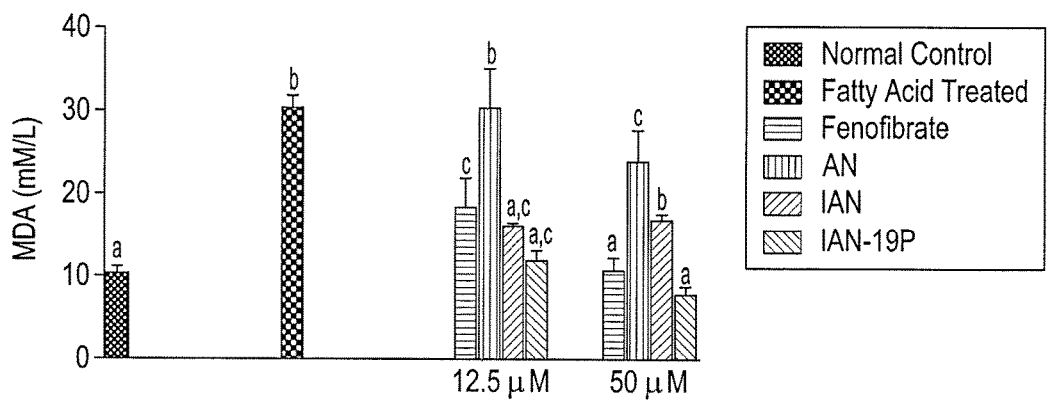
FIG. 4 is a chart showing the effect of AN, IAN and IAN-19P on lipoperoxide formation of palmitate-oleate induced HepG2 cell lines.
Figure 5:
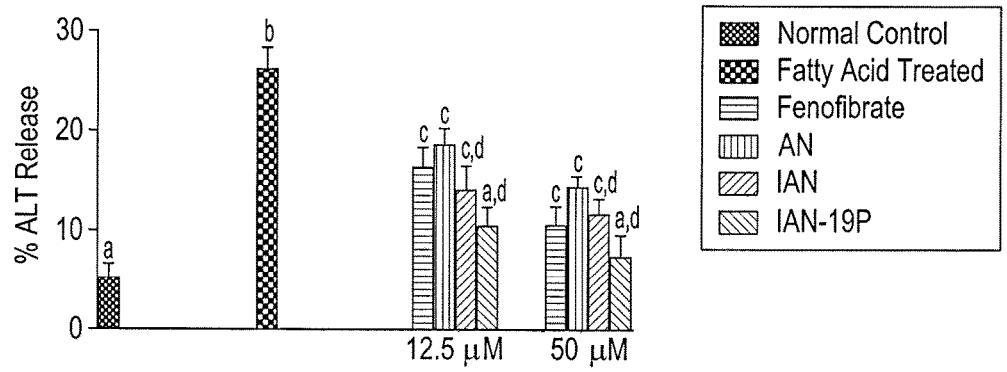
FIG. 5 is a chart showing the effect of AN, IAN and IAN-19P on ALT leakage of palmitate-oleate induced HepG2 cell lines.

Note, in FIGS. 3-5, values indicate mean±SD for three independent experiments; normal, disease control, fenofibrate and test compounds at same dose level were compared and values having the same alphabets among them did not vary significantly (Tukey's HSD; P≤0.005)

It is to be understood that the isoandrographolide-19-propionate for treatment of non-alcoholic fatty liver disease (NALFD) is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound named isoandrographolide-19-propionate, having the formula:

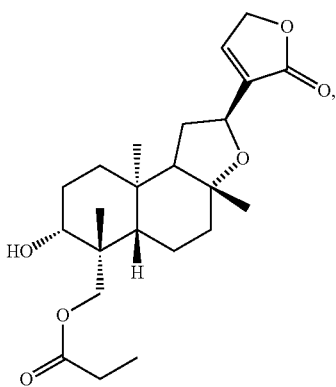

and pharmaceutically acceptable salts thereof.

2. A pharmaceutical agent for reducing the incidence of non-alcoholic fatty liver disease, comprising a pharmaceutical composition having the compound of claim 1 as its active ingredient.

3. A pharmaceutical agent for treatment of non-alcoholic fatty liver disease and hepatocellular disorders and diseases incident thereto, comprising a pharmaceutical composition having the compound of claim 1 as its active ingredient.

4. A method of making the compound of claim 1, comprising the steps of:
mixing propanoic acid with N,N'-dicyclohexylcarbodiimide (DCC) in dichloromethane to form a mixture; and
adding isoandrographolide and 4-dimethylaminopyridine (DMAP) to the mixture;
monitoring the mixture by thin layer chromatography until reaction between the propanoic acid and the isoandrographolide is complete, thereby obtaining a reaction product;
packing a chromatography column with the reaction product;
eluting the packed chromatography column first with hexane, then with a mixture of hexane and dichloromethane, and then with a mixture of 5% methanol in dichloromethane; and
recovering isoandrographolide-19-propionate from the elutant of the mixture of 5% methanol in dichloromethane.

5. A method of making isoandrographolide-19-propionate, comprising the steps of:
mixing propanoic acid with N,N'-dicyclohexylcarbodiimide (DCC) in dichloromethane to form a mixture; and
adding isoandrographolide and 4-dimethylaminopyridine (DMAP) to the mixture;
monitoring the mixture by thin layer chromatography until reaction between the propanoic acid and the isoandrographolide is complete, thereby obtaining a reaction product;
packing a chromatography column with the reaction product;
eluting the packed chromatography column first with hexane, then with a mixture of hexane and dichloromethane, and then with a mixture of 5% methanol in dichloromethane; and
recovering isoandrographolide-19-propionate from the elutant of the mixture of 5% methanol in dichloromethane.

6. The method of making isoandrographolide-19-propionate according to claim 5, further comprising the steps of:
adding concentrated HCl to andrographolide to obtain a mixture;
stirring the mixture at room temperature for 24 hours;
pouring the stirred mixture into ice cold water to cool the mixture
extracting the cooled mixture with dicholoromethane to obtain an organic layer;
washing the organic layer with water and drying the washed organic layer over anhydrous $Na_2SO_4$, and
recrystallizing the dried organic layer with dichloromethane to yield the isoandrographolide.

7. A method of treating non-alcoholic fatty liver disease, comprising the step of administering an effective amount of a pharmaceutical agent to a patient in need thereof, the pharmaceutical agent including isoandrographolide-19-propionate, having the formula:

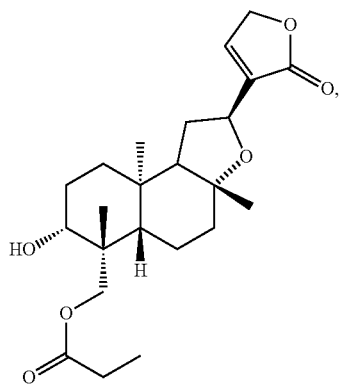

or a pharmaceutically acceptable salt thereof.

* * * * *